US009359396B2

(12) United States Patent
Chaix et al.

(10) Patent No.: US 9,359,396 B2
(45) Date of Patent: Jun. 7, 2016

(54) MATERIAL FOR SUPPORTED SYNTHESIS AND METHOD FOR GROWING OLIGONUCLEOTIDES OR PEPTIDES

(75) Inventors: Carole Chaix, Chaponnay (FR); Gabriel De Crozals, Lyons (FR); Carole Farre, Lyons (FR)

(73) Assignees: UNIVERSITE CLAUDE BERNARD LYON I, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 248 days.

(21) Appl. No.: 14/131,490

(22) PCT Filed: Jul. 10, 2012

(86) PCT No.: PCT/FR2012/051628
§ 371 (c)(1),
(2), (4) Date: Jan. 8, 2014

(87) PCT Pub. No.: WO2013/007944
PCT Pub. Date: Jan. 17, 2013

(65) Prior Publication Data
US 2014/0135478 A1  May 15, 2014

(30) Foreign Application Priority Data
Jul. 12, 2011  (FR) .................................. 11 56338

(51) Int. Cl.
*C07K 1/04* (2006.01)
*B05D 7/00* (2006.01)
*C07H 21/00* (2006.01)
(Continued)

(52) U.S. Cl.
CPC . *C07K 1/042* (2013.01); *B05D 7/00* (2013.01); *C07H 21/00* (2013.01); *B01J 2219/00632* (2013.01); *B01J 2219/00641* (2013.01); *B01J 2219/00722* (2013.01); *B05D 1/185* (2013.01);
(Continued)

(58) Field of Classification Search
None
See application file for complete search history.

(56) References Cited

U.S. PATENT DOCUMENTS

2005/0191686 A1  9/2005 Han et al.

FOREIGN PATENT DOCUMENTS

WO   03/048769   6/2003
WO   2006/073495  7/2006

OTHER PUBLICATIONS

Mukherjee, Entrapment and catalytic activity of gold nanoparticles in aminefunctionalized MCM-41 matrices synthesized by spontaneous reduction of aqueous chloroaurate ions, 2001.*
Y. Cheng et al., "Fluorescence Near . . . DNA Sensing", Analytical Chemistry, 83 (2011) 1307-1314.
G. De Crozals et al., "Oligonucleotide solid-phase . . . pore glass", RSC Advances, 2012, 2, 11858-11866.
(Continued)

*Primary Examiner* — Melvin C Mayes
*Assistant Examiner* — Stefanie Cohen
(74) *Attorney, Agent, or Firm* — Clark & Brody

(57) ABSTRACT

The invention concerns a material composed of a porous support on which functionalized nanoparticles are grafted by covalent bonding, characterized in that at least part of the nanoparticles grafted by covalent bonding is housed inside surface pores of the support, and in that the support is silica-based and is in the form of porous particles of heterogeneous shape and size, the size of the particles being larger than 1 μm and preferably within the range of 5 to 200 μm.
The invention further concerns a growth method for oligonucleotides or peptides characterized in that growth is performed on a material formed of a porous support on which functionalized nanoparticles are grafted by covalent bonding, characterized in that at least a part of the nanoparticles grafted by covalent bonding is housed inside surface pores of the support.

28 Claims, 4 Drawing Sheets

(51) Int. Cl.
 *B05D 1/18* (2006.01)
 *B05D 7/22* (2006.01)
 *B82Y 30/00* (2011.01)
(52) U.S. Cl.
 CPC . *B05D 7/22* (2013.01); *B82Y 30/00* (2013.01); *Y10T 428/2982* (2015.01)

(56) References Cited

OTHER PUBLICATIONS

C. Farre et al., "Automated Oligonucleotide . . . Particle Supports", Langmuir Article, (2010) 26(7) 4941-4950.

* cited by examiner

MATERIAL FOR SUPPORTED SYNTHESIS AND METHOD FOR GROWING OLIGONUCLEOTIDES OR PEPTIDES

FIELD OF THE INVENTION

The present invention concerns the technical field of materials suitable for performing solid-phase synthesis and more specifically materials suitable for acting as synthesis support in automated synthesizers for oligonucleotides or peptides.

BACKGROUND ART

Nanoparticles having a size of the order of 2-100 nm in particular are the focus of increasing intention for applications in imaging and diagnosis since they offer a very large specific surface area, the increase in the surface area of a sphere being proportional to the square of its radius. In addition, for in vivo applications the mechanisms of diffusion in tissues and the cell entry of nanoparticles differ from those of objects of larger size which are rapidly eliminated by the body. For such applications it is often necessary for these nanoparticles to be carriers of oligonucleotides or peptides. Within this context, the inventors of the present patent application have turned to the issue of preparing nanoparticles as support for conducting solid-phase synthesis requiring chain reactions, as is the case in particular for the synthesis of oligonucleotides or peptides.

It is difficult to couple peptides or oligonucleotides onto nanoparticles since the latter are difficult to sediment at the bottom of a tube (by centrifugation). Their replacing in solution is also very difficult and may give rise to problems of irreversible aggregation. In addition, the conformations (or three-dimensional structures) taken on by biomolecules in solution frequently cause strong steric hindrance around the reactive functions required for grafting onto nanoparticles. On this account, the coupling yields of biomolecules on objects of nanometric size are low. In the literature the highest grafting densities of biomolecules obtained using coupling techniques are of the order of 0.01-0.05 oligonucleotides/$nm^2$ (Y. Cheng, T. Stakenborg, P. V. Dorpe, L. Lagae, M. Wang, H. Chen, G. Borghs, Anal Chem, 83 (2011) 1307-1314).

Additionally, automated solid-phase synthesis cannot be envisaged at the current time on nanoparticles since this strategy requires confinement of the nanoparticles in synthesis cells closed by porous filters of sintered type or porous diaphragms which raises two major problems. First, the minimum size of the pores of porous filters required so that the synthesis solvents and reagents are able to enter the synthesis cell without modifying the pressure of the circuit in which the solvents and reagents circulate (in general no more than 4 to 6 bars) is 2 to 4 µm. A smaller pore size for the porous filters would generate an increase in pressure leading to slower flow rates, to fouling of the surface of the support materials and hence to synthesis of poor quality. Also, there does not exist a porous filter which is both resistant to the organic solvents used for such synthesis (which are generally acetonitrile, dichloromethane, pyridine, tetrahydrofuran, . . . ) and which has a pore size of less than one micron.

In an endeavour to solve this issue, some of the inventors of the present patent application have proposed confining the nanoparticles by immobilising them temporarily on silica microparticles. Therefore, the inventors have already proposed assemblies called NOMs (Nano-on-Micro) formed of silica particles of micrometric size (2 to 4 µm) and of spherical shape coated with a monolayer of nanoparticles which offer an overall size of more than 4 µm, a size that is theoretically compatible with the strategy of automated solid-phase synthesis. Syntheses of fragments of deoxyribonucleic acids (DNA) have been successfully conducted (Farre et al., Langmuir, 2010, 26(7), 4941-4950, C. Farre, M. Lansalot, R. Bazzi, S. Roux, C. A. Marquette, G. Catanante, L. J. Blum, N. Charvet, C. Louis, C. Chaix, Langmuir, (2010) 26(7) 4941-4950).

Nevertheless, the proposed NOMs do not allow some difficulties to be overcome. First, the NOMs still of size that is too small, have a tendency to clog the filters and cannot properly be replaced in suspension between the synthesis steps. In addition, the mechanical friction applied to the NOMs by the flows of argon and the passing of the different reagents and solvents used for synthesis (which strongly agitate the particles) leads to the detachment of a large number of nanoparticles during synthesis. For example, it has been observed by some of the inventors that there is loss of nanoparticles during synthesis as well as poor quality of oligonucleotide syntheses on the nanoparticles.

SUMMARY OF THE INVENTION

The present invention therefore proposes a solution with which to overcome these drawbacks. The invention concerns a material composed of a porous support on which functionalized nanoparticles are grafted by covalent bonding and in which at least a portion of the nanoparticles grafted by covalent bonding is housed inside the surface pores of the support. This support is silica-based and is in the form of porous particles of heterogeneous shape and size, the size of the particles being larger than 1 µm, and preferably within the range of 5 to 200 µm. These particles are preferably formed of silica or a silicate. The size of the particles is defined as their largest size and can be measured using a scanning electron microscope or optical microscope. The size of the objects of heterogeneous shape is defined as the length of the longest side of the object. For example, a non-spherical particle having a maximum length of 10 µm, and maximum width and depth (height) of 5 µm will be characterized by a size of 10 µm.

A further subject of the present invention is a method for growing oligonucleotides or peptides wherein growth is performed on a material formed of a porous support on which functionalized nanoparticles are grafted by covalent bonding, characterized in that at least a part of the nanoparticles grafted by covalent bonding is housed inside surface pores of the support.

Preferably, the support used corresponds to a support according to the invention. Said support is preferably a silica-based mineral glass. One example of a silica-based support corresponds to a support containing a silicate. In particular the support is composed exclusively of silica or is composed exclusively of a silicate in which the silica is in a mixture with another or other oxides such as $B_2O_3$ to form borosilicates or $Al_2O_3$ to form aluminosilicates, optionally in a mixture with $Na_2O$.

DETAILED DESCRIPTION OF THE INVENTION

Figure 2:
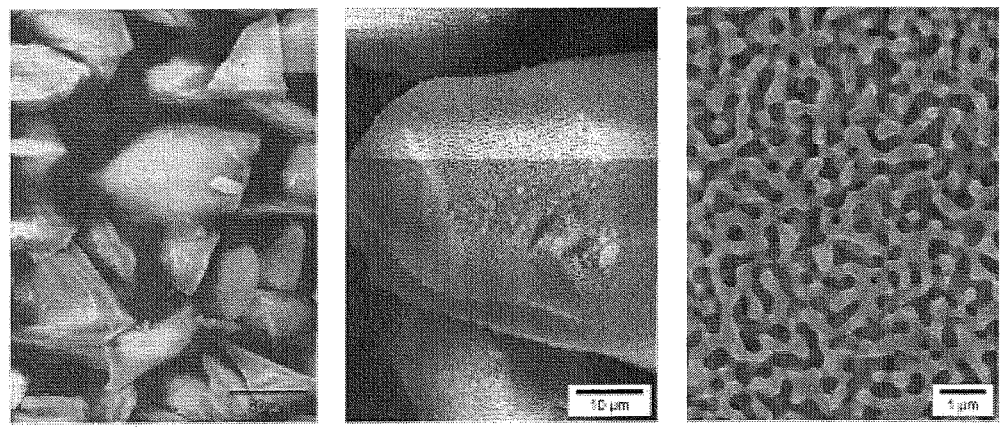
FIG. 2 shows photographs of a CPG support (Fluka-CPG 3000, Ref 27732) taken under scanning electron microscope with different magnifications.

A glass material with controlled porosity called CPG (Controlled Pore Glass) described in particular in Masad J. Damha et al. in Nucl. Acids Res. (1990)18(13), 3813-3821, M H Caruthers, in Science (1985) 18 (230), 281-285, Gelb L. D., Gubbins K. E., Characterization of porous glasses: Simulation models, adsorption isotherms, and the Brunauer-Emmet-Teller analysis method, Langmuir (1998), 14, 2097-2111 and Lit. No DS1007EN00 Rev. B on the Millipore site www.millipore.com can be used as support for immobilising nanoparticles. This material is conventionally used for the automated solid-phase synthesis of nucleic acid fragments. It is formed of small particles of silica of most heterogeneous shape. On the other hand, the pore size is controlled. It is possible for example to use the CPG described in documents U.S. Pat. No. 346,608 and U.S. Pat. No. 3,549,524, by Köster H. et al. in Tetrahedron (1984) 40 (1), 103-112 or those made available by Millipore. FIG. 2 shows photographs of a CPG support (Fluka-CPG 3000, Ref 27732) taken under scanning electron microscope with different magnifications.

It can also be envisaged that the support used in the invention is a polymer such as a polystyrene-co-divinylbenzene or polypropylene-co-divinylbenzene polymer. Nevertheless, supports in mineral glass and particularly in CPG are preferred, since polymer materials may carry risks of swelling and hence lesser control over porosity.

Figure 1:
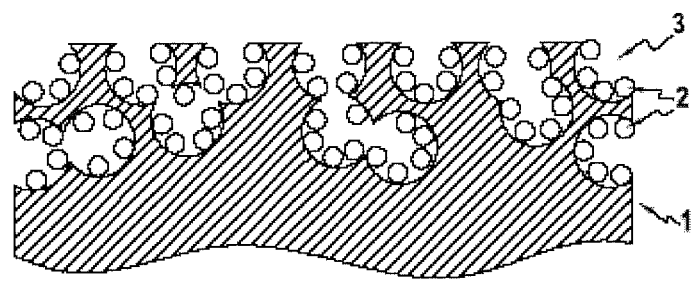
FIG. 1 schematically illustrates a material of the invention.

FIG. 1 schematically illustrates a material of the invention in which the support carries reference 1, the nanoparticles are referenced 2 and the pores are referenced 3. The grafting of the nanoparticles inside the pores of the support protects them against mechanical friction resulting from the passing of synthesis fluids and argon flows in the synthesis cells during synthesis operations. However, the nanoparticles remain accessible since, although they are housed inside the pores of the support, they remain close to the surface of the support in the pores lying on the surface of the support even if some are able to enter deeper into the bulk of the support. The so-called surface pores can be seen on the surface of the support and form holes or openings on the support surface. The cavities or channels corresponding to said pores are therefore accessible from the surface of the support.

Advantageously, irrespective of the support and nanoparticles used, the mean minimum size of the surface openings formed by the surface pores of the support is at least 3 times, preferably 5 to 30 times equal to the mean size of the nanoparticles. Therefore, there still remains within the pores sufficient volume to carry out the desired solid-phase syntheses.

By mean minimum size of the surface openings formed by the surface pores is meant the arithmetical mean of 50 measurements of the smallest size of the surface openings corresponding to the pores which can be seen in an image of the support taken under scanning electron microscopy. The arithmetical mean is therefore calculated from the measurements of the smallest size in an image of 50 pores visible on the surface of the support.

The mean size of the nanoparticles corresponds to the arithmetical mean of the largest size or of the longest side of 50 nanoparticles measured under transmission electron microscopy, previously calibrated, after detachment of the said nanoparticles from the support by specific treatment adapted to cleave the covalent bond formed between the support and the nanoparticles, as detailed below. For example, treatment with 1% ammonia solution is applied to cleave an ester bond. After detaching the nanoparticles and neutralising residual ammonia with an acid e.g. a solution of acetic acid, a few microliters (typically 1 to 5 µL) of solution of nanoparticles are deposited and left to dry in open air on a grid adapted for observation under transmission electron microscopy (for example a copper or nickel grid coated with Formvar (polyvinyl formol), with collodion (cellulose nitrate) or carbon or collodion-carbon mixture). Most often, the nanoparticles used are essentially spherical i.e. their shape does not deviate more than 10% from a perfect sphere. It is also possible that the nanoparticles are in the form of nanotubes. In this case, their largest size corresponds to their length.

Advantageously, the support used has at least one of the following characteristics or any combination of these characteristics:

- the mean diameter of the pores of the support used lies in the range from 30 to 600 nm, preferably in the range of 100 to 400 nm. The mean diameter of the pores of the support is measured using a mercury intrusion method or nitrogen adsorption technique as per standard ISO 15901 (Distribution of pore dimensions and porosity of solid materials by mercury porosimetry and gas adsorption) the mercury intrusion method being preferred;
- the support has homogeneous porosity corresponding to the fact that at least 80% of the pores have a diameter whose value does not vary more than 10% compared to the mean diameter of the pores;
- the support has a pore volume per gram of 0.5 to 2 mL/g;
- the support has a specific surface area within the range of 5 to 80 $m^2/g$, which allows the grafting of a high number of nanoparticles per unit surface area.

By specific surface area is meant the B.E.T. specific surface area determined by nitrogen adsorption conforming to standard ASTM D 3663-78 based on the BRUNAUER-EMMETT-TELLER method described in the journal "The Journal of the American Chemical Society, 60, 309 (1938)".

CPGs, such as previously defined, are materials of choice for exhibiting all of these characteristics.

Advantageously, the nanoparticles immobilised by covalent bonding on the support and at least a portion thereof on the surface of the support pores so as to be housed preferably fully housed therein, have at least one of the following characteristics or any combination of these characteristics:

- the nanoparticles have a mean size in the range of 2 to 100 nm;
- the nanoparticles are nanoparticles of silica, gold, silver, graphite, fluorescent nanocrystals (also called quantum dots), polymer nanoparticles of polystyrene, polypropylene or polybutadiene type, or metal oxide nanoparticles in particular tin, gadolinium, aluminium, titanium, cerium, niobium, erbium, ytterbium, terbium, dysprosium, europium oxides, or a mixture of these oxides, optionally coated to allow the functionalization thereof;
- at least 80%, and preferably at least 90% of the grafted nanoparticles are directly bonded by covalent bonding to the support i.e. without any intermediate nanoparticle ensuring the said bonding;
- the nanoparticles are functionalized by reactive functions chosen from among alcohols, amines and thiols allowing the growth of oligonucleotides or peptides. By this it is meant that the nanoparticles carry hydrocarbon arms able to contain one or more heteroatoms chosen in particular from among N and O, and terminating in a —OH, $NH_2$ or SH function respectively;

the nanoparticles are functionalized with free hydrophilic organic molecules chosen for example from among polyethylene glycol, polyethylamine, . . . or with fluorescent organic molecules such as fluorescein, rhodamine, cyanines;

the nanoparticles are functionalized by covalent bonding with biological ligands chosen from among peptides and oligonucleotides. According to one particular embodiment, the material of the invention has a high density of biological ligands grafted on the surface of the nanoparticles corresponding to more than 0.1 molecule of biological ligand per $nm^2$ of nanoparticles. However, some applications may require a lower grafting density. In this case grafting could be less extensive for example by reducing the incorporation yields of the first peptide or nucleotide monomer, during the synthesis of the biomolecule. Having regard to the fact that the nanoparticles during the growth of the biological ligands are attached onto a support, the nanoparticles carrying biological ligands that are obtained are most often dissymmetric which means that at least 90% of the biological ligands are grafted on a continuous region representing less than 70% of the surface of the nanoparticle on which they are grafted.

Preferably, the materials of the invention combine the characteristics mentioned below or in the remainder of the description for the support, and those mentioned below or in the remainder of the description for the nanoparticles.

According to preferred embodiments which can be combined with the preceding embodiments the nanoparticles are grafted on the support by a bond that can be cleaved under mild conditions e.g. an ester bond, alkoxysilyl bond, a disulphide bridge, 4-(2-hydroxyethyl)-3-nitrobenzoic acid bond, N-[9-(hydroxymethyl)-2-fluorenyl]succinamic acid bond, thiophosphoramidatehydroxypropyl bond or an amide bond activated by a 2-propane diol group. Said bonds are table under the conditions subsequently applied during solid-phase synthesis of oligonucleotides or peptides in particular, and can later be cleaved under mild conditions i.e. conditions which do not deteriorate the molecules grafted on the surface of the nanoparticles and will not cleave the covalent bonds existing between these molecules and the nanoparticles. The molecules of interest and in particular the biological ligands are grafted onto the nanoparticles by a covalent bond resulting from the coupling of the first phosphoramidite nucleoside, for oligonucleotide synthesis, on the reactive functions present on the surface of the nanoparticles and in particular of amine, thiol or alcohol type. The covalent bond resulting from this coupling corresponds to a phosphoramidate diester or phosphorothioate diester or phosphate diester. This covalent coupling between the nanoparticles and the molecules grafted thereupon (and in particular the biological ligands) does not use the same type of bonding as those used to bind the nanoparticles to the support.

In particular, the grafting of the nanoparticles on the support in particular of CPG type can take place via an ester bond which is cleavable in a base medium. For this purpose, the nanoparticles are functionalized with alcohol arms having a hydroxyterminal function and the support with acid functions.

In particular, in the invention the covalent bond between the nanoparticles and the support can be obtained by coupling between an arm having an acid terminal function positioned on the support, chosen among: —(CH2)n-NH—CO—(CH2)m-COOH, —(CH2)n-COOH, —(CH2)n-NH—(CH2)m-COOH, with n being an integer in the range of 2 to 18 and m being an integer in the range of 2 to 6, and an arm having an alcohol terminal function positioned on the nanoparticles chosen among:

—(CH2)q-NH—CO—NH—(CH2)r-OH, —(CH2)s-OH, —(CH2)q-O—[(CH2)2-O]p-H and —(CH2)q-CONH—(CH2)r-OH, —(CH2)q-NH—(CH2)r-OH, —(CH2)q-CHOH—CH2-NH—(CH2)p-OH, —(CH2)q-[CH—(CH2OH)]—NH—(CH2)p-OH, —(CH2)q-CHOH—CH2-O—(CH2)p-OH, —(CH2)q-[CH—(CH2OH)]—O—(CH2)p-OH, —(CH2)q-CHOH—CH2-O—CO—NH—(CH2)p-OH with s being an integer in the range of 2 to 18, p being an integer in the range of 1 to 6, q being an integer in the range of 1 to 12, and r being an integer in the range of 1 to 12.

Since the arms on the nanoparticles do not all react with the arms present on the support to form an ester bond, there remain free arms on the surface of the nanoparticles which will be able to react with the peptide or oligonucleotide monomers subsequently used to perform peptide and oligonucleotide syntheses.

Other types of bonds that can be cleaved under mild conditions can also be envisaged:

an alkoxysilyl bond resulting from the reaction of an alcohol arm on OH functions present on the surface of the support (in particular silanols if CPGs are used) which are cleaved under base conditions (Farre, C. et al., Langmuir, 2010, 26(7), 4941-4950);

an oxalyl bond resulting from the reaction of oxalic acid and an alcohol arm which is cleaved in a base medium (Pon, R. et Yu S., Nucl. Acids Res., 1997, 25, 18, 3629-3635);

a disulphide bridge or disulphide bond resulting from the reaction of two thiol functions and which is cleaved in a reducing medium (DTT) (Asseline, U. et al., Tetrahedron, 1992, 48, 1233-1254.);

a thiophosphoramidatehydroxypropyl bond resulting from a reaction between an amine function and a hydroxypropylphosphoramidite group followed by oxidation of the phosphite formed by a sulphur and which is cleaved at 90° C. under neutral conditions (Grajkowski, A. et al., Bioconjugate, Chem. 2008, 19, 1696-1706);

an amide bond activated by a 2-propane diol group which is cleaved under base conditions (Ref: Azhayev, A. V. et al., Tetrahedron, 2001, 57, 4977-4986).

For the modification and functionalization of the supports, reference can be made to: Current Protocols in Nucleic Acid Chemistry, Volume 1, Editors: S. L. Beaucage, D. E. Bergstrom, G. D. Glick, R. A. Jones, John Wiley & Sons, Inc., 2004. For the synthesis of silica nanoparticles, reference can be made to the article by Zou H., Wu S. and Shen J., Polymer/silica nanocomposites: preparation, characterization, properties and applications, Chem. Rev. (2008), 108(9), 3893-3957 and to the book by Bergna, H. E. and Roberts, W. O., Colloidal silica fundamentals and applications, Surfactant Science Series, Vol. 131, Taylor & Francis, CRC Press Book, 2006. For the modification and functionalization of silica nanoparticles, reference can be made to the articles by Oh, S. J., Hong, B. J., Choi, K.Y. and Park J. W. Surface modification for DNA and protein microarrays, OMICS, A journal of Integrative Biology, 2006, 10, 327; Trewyn, B. G., Slowing, I. I., Giri, S., Chen, H.-T., Lin, V. S.-Y. Synthesis and functionalization of a mesoporous silica nanoparticle based on the sol-gel process and applications in controlled release, Acc. Chem. Res., 2007, 40, 846-853; and for the functionalization of particles of metal or metal oxide the article by Neouze, M.-A., Schubert, U., Surface modification and functionalization of metal and metal oxide nanoparticles by organic ligands, Monatsh, Chem., 2008, 139, 183-195. In particular, if the nanoparticles are silica nanoparticles, the —OH reactive functions used will not correspond to the silanol functions directly present on the surface of the silica nanoparticles or obtained after activation by an acid or base for example, these subsequently not allowing bonds to be obtained that are sufficiently stable with the biomolecules of interest, of peptide or oligonucleotide type in particular. For oligonucleotide synthesis, these silanol functions will be modified by reaction with an alkoxysilane group carrying an —OH terminal function which itself will be coupled to a phosphoramidite nucleoside to form a stable phosphate diester bond. For peptide synthesis, the —OH terminal functions of the nanoparticles will be modified to —$NH_2$ functions by reaction of a C3, C6, C12 or other amino alkyl phosphoramidite, such as marketed by Glen Research (Sterling, Va., USA). These —$NH_2$ functions will allow the initiating of peptide synthesis by reaction of a reactive amino acid to form a peptide bond (—NH—CO). Some CPGs already functionalized with carboxylic acid or amine functions are marketed for example by PureBiotech LLC (752A Lincoln Blvd. Middlesex, N.J. 08846). It is possible for example to use LCAA-CPG (Long Chain Alkylamine Controlled Pore Glass), marketed by Millipore (290 Concord Road, Billerica, Mass. 01821), which is conventionally used for oligonucleotide synthesis. LCAA-CPG is functionalized with amine functions which can be transformed to a carboxylic acid function, for example by reaction with succinic anhydride.

Advantageously the solvent used for grafting of the nanoparticles on the support is a solvent in which the nanoparticles are stable i.e. not aggregated. The use of a said solvent allows homogenous coating of the support with individualised nanoparticles. For silica nanoparticles, dimethylformamide (DMF) could be used for example.

The grafting of the nanoparticles takes place both inside the pores and close to the surface of the support. However, in the invention the advantage lies in the fact that at least a portion of the particles is grafted covalently inside the pores of the support surface whilst remaining accessible and will therefore be subsequently protected when the particles are subjected to mechanical stress, thereby preventing their detachment.

Before using the support thus obtained, having nanoparticles covalently grafted inside surface pores, it is most often preferable to neutralise or deactivate the residual reactive functions present on the surface of the support. Such techniques are known to persons skilled in the art. For example, for carboxylic acid functions, these can be blocked by action of piperidine to prevent the initiating of subsequent parasitic reactions on the surface of the support.

After coupling between the nanoparticles and the support, there remain free reactive functions on the surface of the nanoparticles which will be able to react, within an automated synthesizer cell, with the first peptide or oligonucleotide brick (also called monomer) allowing the synthesis of the desired peptides or oligonucleotides. Most often, these reactive functions which will allow the attaching of the $1^{st}$ nucleotide or $1^{st}$ amino acid are the same as those which allowed the covalent bonding of the particles onto the support. Nevertheless, two different reactive functions could be provided on the surface of the nanoparticles, some to allow their grafting onto the support, others for the subsequent grafting of the molecules of interest. Since the nanoparticles are grafted onto the support, only part of their surface will be accessible and able to be covalently bonded with the desired peptides or oligonucleotides. In general, the nanoparticles obtained are dissymmetric with at least 90% of the biological ligands grafted on a continuous region representing less than 70% of the surface of the nanoparticle on which they are grafted.

The material of the invention is therefore fully suitable for performing solid-phase synthesis of oligonucleotides or peptides in particular. The main advantage of solid-phase synthesis is that it allows the grafting on the surface of an object of functional blocks using a basic support, as desired and in customised manner. Another advantage of solid-phase synthesis is the perfect control over the orientation of the grafted biomolecules.

As previously indicated, a further subject of the invention is a method for growing oligonucleotides or peptides whereby growth is conducted on a material formed of a porous support on which functionalized nanoparticles are grafted by covalent bonding, characterized in that at least a portion of the nanoparticles grafted by covalent bonding is housed inside surface pores of the support. Advantageously such growth is conducted in an automated synthesizer in which the support is confined in a cell by means of a filter through which flows of argon and reagents circulate alternately. Before the growth operation, there are also nanoparticles grafted covalently on the outer surface of the support or outside the pores, but these for the most part are eliminated after reaction in the synthesizer by the flows of argon and reagents, only the nanoparticles located inside the pores being maintained. Conventional methods for the synthesis of peptides and oligonucleotides in an automated synthesizer can be implemented. For further details on the automated synthesis of oligonucleotides, reference can be made to the book: Current Protocols in Nucleic Acid Chemistry, Volume 1, Editors: S. L. Beaucage, D. E. Bergstrom, G. D. Glick, R. A. Jones, John Wiley & Sons, Inc., 2004. For further details on the automated synthesis of peptides, reference can be made to the article by Amblard, M., Fehrentz, J.-A., Martinez, J., Subra, G., Methods and protocols of modern solid phase peptide synthesis, in Molecular Biotechnology, 2006, 33, 239-254.

Most often, once growth is completed the covalent bond between the support and the nanoparticles is cleaved. For example for an ester bond, cleavage can be performed in a basic medium e.g. in a 1% solution of $NH_4OH$ at 60° C. For other envisaged bonds, reference can be made to the publications cited above which detail the cleavage conditions which can be used.

In the invention, the term <<oligonucleotide>> designates a sequence of at least 2 nucleotides (deoxyribonucleotides or ribonucleotides, or both), natural or modified, able to hybridise under suitable hybridisation conditions with an oligonucleotide that is complementary at least in part. By nucleotide is meant an organic compound formed of a purine or pyrimidine base bonded to an ose (ribose or deoxyribose) and to a phosphate group. By modified nucleotide is meant for example a nucleotide comprising a modified base and/or comprising a modification at the inter-nucleotide bond and/or at the backbone. As an example of modified base, mention can be made of inosine, methyl-5-deoxycytidine, dimethylamino-5-deoxyuridine, diamino-2,6-purine and bromo-5-deoxyuridine. To illustrate a modified inter-nucleotide bond mention can be made of phosphorothioate, N-alkylphosphoramidate, alkylphosphonate and alkylphosphotriester bonds. The alpha-oligonucleotides such as those described in FR-A-2 607 507 and the PNAs which are the subject of the article by M. Egholm et al., J. Am. Chem. Soc. (1992), 114, 1895-1897, are examples of oligonucleotides formed of nucleotides whose backbone has been modified.

The term <<peptide>> particularly designates any sequence of at least two amino acids such as protein, protein fragment, oligopeptide which has been extracted, separated, isolated or synthesised such as a peptide obtained by chemical synthesis or by expression in a recombinant organism. Also included are all the peptides in whose sequence one or more amino acids of the L series are replaced by one or more amino acids of the D series and vice-versa; any peptide of which at least one of the CO—NH bonds is replaced by a NH—CO bond; any peptide of which at least one of the CO—NH bonds is replaced by a NH—CO bond, the chirality of each aminoacyl residue whether or not involved in one or more of the said CO—NH bonds, being either preserved or reversed compared with the aminoacyl residues forming a reference peptide (or immunoretroids); and any mimotope.

In the invention, it is therefore possible to prepare nanoparticles functionalized with peptides or oligonucleotides, but also with other molecules of fluorescent molecule type. Said nanoparticles, through the very nature of the nanoparticle and the elements they may incorporate, can act as markers or tracers particularly in in vivo applications. The nanoparticles obtained may be fluorescent, radioactive, conductive, magnetic, may be used a MRI contrast agents . . . .

Different variants can be made to the invention. In particular, it is possible to use the same functions present on the nanoparticles both to carry out the grafting thereof on the support and later to carry out growth of the peptides or oligonucleotides. It could also be envisaged to use different functions, for example by successively grafting different functional blocks on the surface of the nanoparticles.

1. Activation of the Surface of the CPG Support by Nitric Acid

The CPG used was CPG 3000 (Fluka-Ref 27732). For CPG 3000, the mean diameter of the pores given by the manufacturer is about 300 nm±75 nm, which corresponds to a standard deviation of 25%.

The activation step of the CPG surface allows the functionalization of the CPG support with silanol groups (SiOH) reacting with the arm which will allows the attaching of the nanoparticles.

2 g of CPG 3000 were heated in 10 mL of 68% nitric acid at 100° C. (rise under reflux) for 1 h. After return to ambient temperature the support was filtered then washed in distilled water to neutral pH of the filtrate. Activation can also be performed in a basic medium for example under the action of aqueous sodium hydroxide.

2. Functionalization of the CPG Support with Primary Amines

The activated CPG obtained at paragraph 1) (2 g) was placed in suspension in 15 mL of a 10% (v/v) aqueous solution of aminopropyltriethoxysilane (APTES) adjusted to pH 4 with hydrochloric acid. The suspension was heated to 70° C. under rotary agitation for 2 h30. After removing the supernatant liquid, the CPG was heated in an oven to 120° C. for 16 h in a ceramic crucible. The CPG was then filtered, washed in acetone and dried in open air.

3. Functionalization of the CPG Support with Carboxylic Acids

The activated CPG obtained at paragraph 2) (2 g) was placed in suspension in 15 mL of a 1M solution of succinic anhydride in acetone with 1% triethylamine (v/v). The suspension was left under agitation for 5 h at ambient temperature. The CPG was filtered, washed in acetone and dried in open air.

Figure 3:
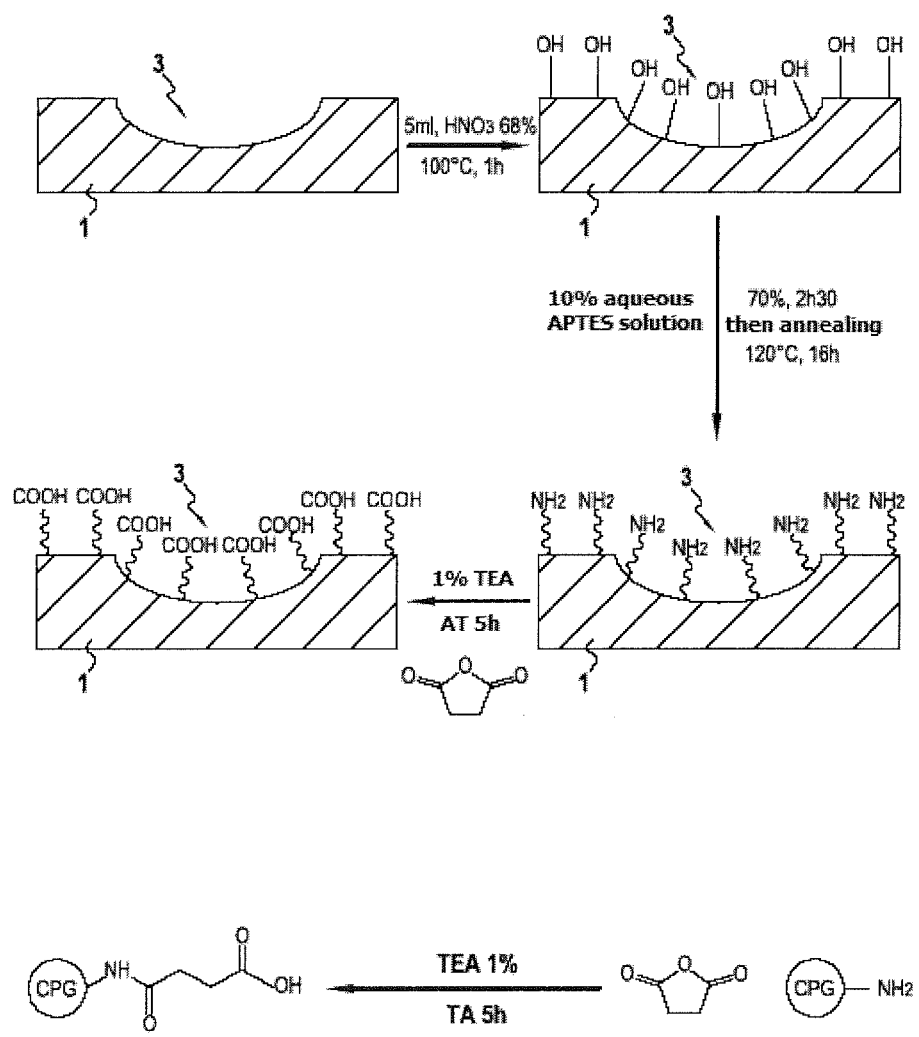
FIG. 3 schematically illustrates the functionalizations obtained at paragraphs 1 to 3 of the examples.

The functionalizations obtained at paragraphs 1 to 3 are schematically illustrated in FIG. 3.

4. Functionalization of the Nanoparticles 4.1 Synthesis of an Alcohol Arm

Aminohexanol (476 mg, 4.06 mmol) and triethoxysilylpropylisocyanate (1 mL, 4.06 mmol) were caused to react in isopropanol in an argon atmosphere and under magnetic stirring at ambient temperature for 30 min. The triethoxysilylpropylhexanolurea alcohol arm thus formed was used without purification.

4.2 Functionalization of the Nanoparticles with the Alcohol Arm

The silica nanoparticles used were supplied by Nano-H (Saint Quentin Fallavier, France). These particles are of core-shell type, the fluorophore being incorporated in the core as described in the article by Burns for cyanine 5 (A. A. Burns, J. Vider, H. Ow, E. Herz, O. Penate-Medina, M. Baumgart, S. M. Larson, U. Wiesner, M. Bradbury, Fluorescent silica nanoparticles with efficient urinary excretion for nanomedicine, Nano Letters (2009) 9(1), 442-448).

A solution of silica nanoparticles, 30 to 70 nm in diameter and carrying Si—OH functions on the surface, in dimethylformamide (C=10 mg of NP/mL) was caused to react with 95 equivalents of silane alcohol previously prepared at paragraph 4.1, and 5 equivalents of 1,2-bis(triethoxysilyl)ethane in the presence of triethylamine. The reaction mixture was brought to 120° C. under reflux for 16 h. After return to ambient temperature, the nanoparticles were purified by centrifugation and re-dispersed in DMF (3 times).

5. Activation of the Carboxylic Acids of the CPG Support

The CPG prepared at paragraph 3 was placed in suspension in anhydrous acetonitrile in the presence of O-(benzotriazol-1-yl)-N,N,N',N'-tetramethyluroniumhexafluorophosphate (HBTU), dimethylaminopyridine (DMAP) and triethylamine. The reaction mixture was left under agitation at ambient temperature for 16 h. The CPG obtained was filtered and washed in DMF.

6. Grafting of the Nanoparticles onto the CPG Support

Figure 4:
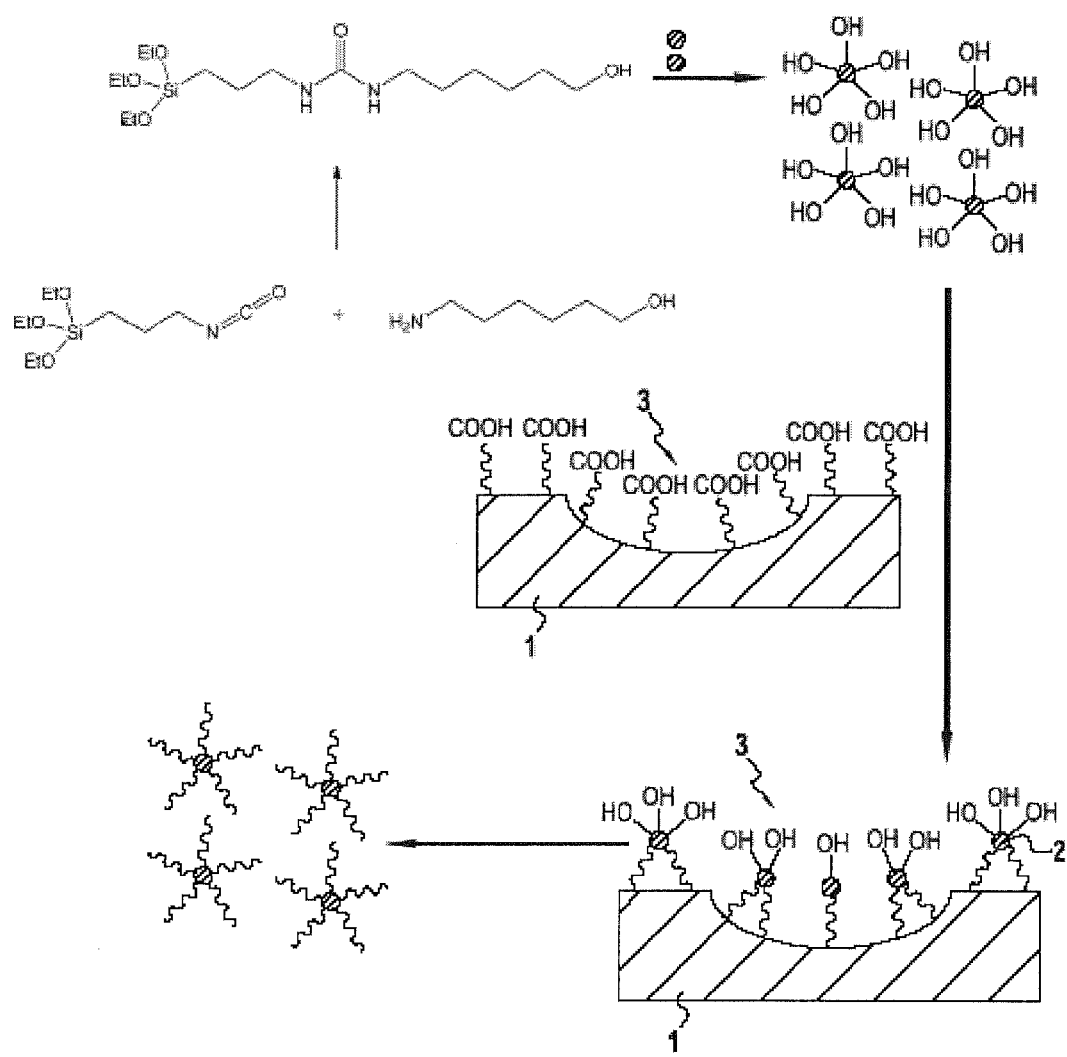
FIG. 4 illustrates the entire method carried out in paragraph 6 of the examples for grafting of the nanoparticles onto the CPG support.

The CPG obtained at paragraph 5 was placed in suspension in anhydrous DMF and the solution of nanoparticles obtained at paragraph 5.2 was added drop-wise. The suspension was left under agitation at ambient temperature for 16 h. The CPG obtained was filtered and washed in DMF and acetonitrile and dried in open air. The entire method carried out is illustrated in FIG. 4.

The carboxylic acids activated by the HBTU/DMAP mixture which did not react with the hydroxyl functions of the nanoparticles were blocked (capped) through the action of piperidine to prevent initiation of parasitic oligonucleotide syntheses on the surface of the CPG.

The CPG was placed insuspension in piperidine and the reaction medium was left under agitation at ambient temperature for several days.

7. Example of the Synthesis of a 23 mer Oligodeoxyribonucleotide on the Nanoparticle-CPG Support Obtained at Paragraph 6

30 mg of nanoparticle-CPG support were placed in a synthesis column installed on an automated synthesizer ABI 394 (AppliedBiosystems).

The sequence of the oligodeoxyribonucleotide was: 5'-ATC TCG GGA ATC TCA ATG TTA GT-3'

The synthesis of the oligodeoxyribonucleotide was performed following the standard 1 µmole programme using the phosphoramidites iPr-Pac-dG, Ac-dC, Pac-dA et dT (Glen Research). The activator used was tetrazole for a coupling time of 60 s. The mean coupling yield per cycle was 97.5%.

Figure 5:
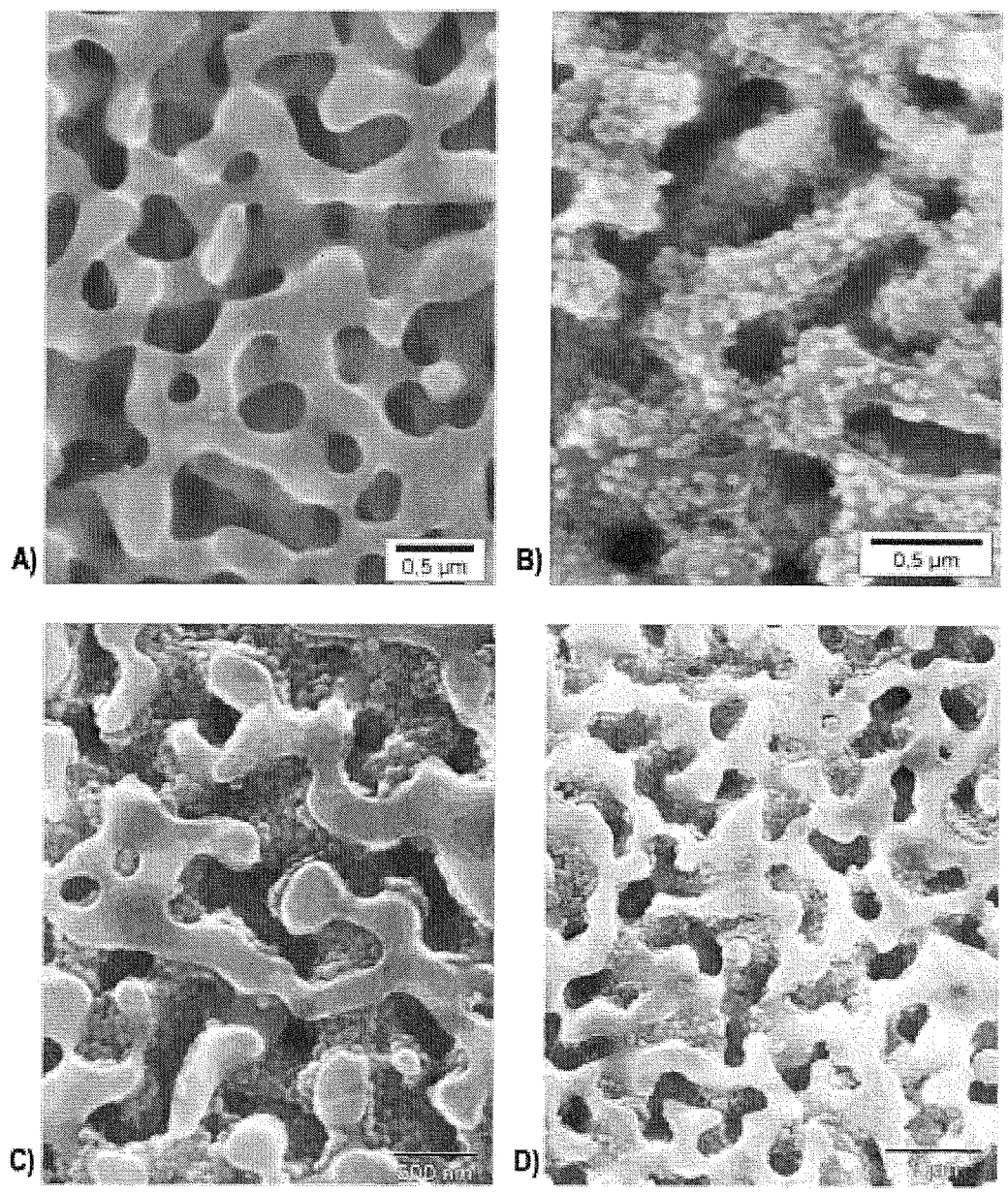
FIG. 5 shows photographs taken under scanning electron microscope of the CPG support of paragraph 7 of the examples: (A) before grafting of the nanoparticles, (B) after grafting of the nanoparticles (C) and (D) after synthesis of the oligonucleotides on the nanoparticles.

FIG. 5 shows photographs taken under scanning electron microscope of the CPG support: (A) before grafting of the nanoparticles, (B) after grafting of the nanoparticles (C) and (D) after synthesis of the oligonucleotides on the nanoparticles. The locating of the nanoparticles inside the pores of the support is clearly evidenced. Before synthesis of the oligonucleotides, there were also nanoparticles on the outer parts of the support (Photo B); however these were eliminated (photos C and D) after reaction in the synthesizer by the flows of argon and reagents, solely the nanoparticles positioned inside the pores being maintained.

8. Example of the Synthesis of a Modified 36 mer Oligoribonucleotide on the Nanoparticle-CPG Support Obtained at Paragraph 6

30 mg of nanoparticle-CPG support were placed in a synthesis column installed on an automated synthesizer ABI 394 (AppliedBiosystems).

The synthesis of the oligoribonucleotide was performed with the standard RNA 1 µmole programme. The coupling step was performed with benzylthiotetrazole (Glen Research), with a coupling time of 240 s. 2'-O-methylpurine and 2'-fluoropyrimidine phosphoramidites were used. The mean coupling yield per cycle was 98.9%.

9. Deprotection of the Oligonucleotides and Detachment of the Nanoparticles.

The oligonucleotides obtained at paragraph 7 or 8 were deprotected with a 0.05 M solution of potassium carbonate in methanol at ambient temperature for a minimum time of 6 hours.

The nanoparticles were then detached from the support through the action of 1% aqueous ammonia (500 µL per 30 mg of support) at 60° C. After 15 to 30 minutes, the nanoparticles were released in solution. The supernatant solution was removed, the ammonia was neutralised by adding a 0.05M solution of acetic acid until a neutral solution was obtained (pH 7).

The number of nanoparticles contained in the solution was estimated by fluorescence emission the nanoparticles used having fluorophores (rhodamine or fluorescein) encapsulated in the silica core.

The number of oligonucleotides on the surface of each particle was evaluated by measuring UV absorbance at 260 nm. Recovery was estimated at between 1000 and 5000 oligos per particle, which corresponds to 0.2 to 1 of oligonucleotides (if one half of the surface of a particle 60 nm in diameter is considered) per $nm^2$ of nanoparticles. Finally, excellent stability of the oligonucleotide-carrying nanoparticles was observed in a PBS buffer and in water. No aggregating of the particles was observed after several weeks in suspension. The high density of the biomolecules present on the surface stabilises the obtained nano-objects in solution.

In addition, the conjugates obtained at paragraphs 8 and 9 proved to be active for targeting the corresponding biological targets (DNA of the hepatitis B virus and protein MMP-9 respectively).

The invention claimed is:

1. A material composed of a porous support on which functionalized nanoparticles are grafted by covalent bonding, characterized in that at least a portion of the nanoparticles grafted by covalent bonding is housed inside surface pores of the support, and in that the support is silica-based and is in the form of porous particles of heterogeneous shape and size, the size of the particles being larger than 1 µm.

2. The material according to claim 1, characterized in that the support is a mineral glass containing silica or a silicate.

3. The material according to claim 1, characterized in that the support is composed exclusively of silica or is composed exclusively of a silicate in which the silica is in a mixture with $B_2O_3$ to form borosilicates or $Al_2O_3$ to form aluminosilicates, optionally in a mixture with $Na_2O$.

4. The material according to claim 1, characterized in that the minimum mean size of the surface openings formed by the surface pores of the support is at least 3 times equal to the size of the nanoparticles.

5. The material according to claim 1, characterized in that the mean diameter of the pores of the support is in the range of 30 to 600 nm.

6. The material according to claim 5, characterized in that the mean diameter of the pores of the support is in the range of 100 to 400 nm.

7. The material according to claim 1, characterized in that the support has homogeneous porosity corresponding to the fact that at least 80% of the pores have a diameter whose value does not vary by more than 10% compared with the mean diameter of the pores.

8. The material according to claim 1, characterized in that the support has a volume of pores per gram of 0.5 to 1.5 mL/g.

9. The material according to claim 1, characterized in that the support has a specific surface area in the range of 5 to 80 $m^2/g$.

10. The material according to claim 1, characterized in that the nanoparticles have a mean size in the range of 2 to 100 nm.

11. The material according to claim 1, characterized in that at least 80% of the grafted nanoparticles are directly bonded by a covalent bond to the support without any intermediate nanoparticles ensuring the said bonding.

12. The material according to claim 11, characterized in that at least 90% of the grafted nanoparticles are directly bonded by a covalent bond to the support.

13. The material according to claim 1, characterized in that the nanoparticles are nanoparticles of silica, gold, silver, graphite, fluorescent nanocrystals, polymer nanoparticles of polystyrene, polypropylene or polybutadiene type, or metal oxide nanoparticles, optionally coated to enable the functionalization thereof.

14. The material according to claim 13, characterized in that the nanoparticles are nanoparticles of tin oxide, gadolinium oxide, aluminium oxide, titanium oxide, cerium oxide, niobium oxide, erbium oxide, ytterbium oxide, terbium oxide, dysprosium oxide or europium oxide, or of a mixture of these oxides, optionally coated to enable the functionalization thereof.

15. The material according to claim 1, characterized in that the nanoparticles are functionalized by reactive functions chosen from among alcohols, amines and thiols allowing the growth of oligonucleotides or peptides.

16. The material according to claim 1, characterized in that the nanoparticles are grafted on to the support by a cleavable bond cleavable under conditions not deteriorating the biological ligands.

17. The material according to claim 16, wherein the cleavable bond is selected from the group consisting of an ester bond, alkoxysilyl bond, disulphide bridge, 4-(2-hydroxyethyl)-3-nitrobenzoic acid bond, N-[9-(hydroxymethyl)-2-fluorenyl]succinamic acid bond, thiophosphoramidatehydroxypropyl bond and an amide bond activated by a 2-propane diol group.

18. The material according to claim 1, characterized in that the covalent bond between the nanoparticles and the support is obtained by coupling between an arm with an acid terminal function positioned on the support, chosen among: —(CH2)n-NH—CO—(CH2)m-COON, —(CH2)n-COOH, —(CH2)n-NH—(CH2)m-COOH, with n being an integer ranging from 2 to 18 and m an integer ranging from 2 to 6, and an arm with an alcohol terminal function positioned on the nanoparticles, chosen among:

—(CH2)q-NH—CO—NH—(CH2)r-OH, —(CH2)s-OH, —(CH2)q-O—[(CH2)2-O]p-Het-CH2)q-CONH—(CH2)r-OH,—(CH2)q-NH—(CH2)r-OH, —(CH2)q-CHOH—CH2-NH—(CH2)p-OH, —(CH2)q-[CH—(CH2OH)]—NH—(CH2)p-OH, —(CH2)q-CHOH—CH2-O—(CH2)p-OH, —(CH2)q-[CH—(CH2OH)]—O—(CH2)p-OH, —(CH2)q-CHOH—CH2-O—CO—NH—(CH2)p-OH with s being an integer ranging from 2 to 18, p an integer ranging from 1 to 6, q an integer ranging from 1 to 12, and r an integer ranging from 1 to 12.

19. The material according to claim 1, characterized in that the nanoparticles are functionalized with free hydrophilic organic molecules or with fluorescent organic molecules.

20. The material according to claim 19, characterized in that the nanoparticles are functionalized with free hydrophilic organic molecules chosen among polyethylene glycol and polyethylamine, or with fluorescent organic molecules chosen among fluorescein, rhodamine and cyanines.

21. The material according to claim 1, characterized in that the nanoparticles are functionalized, by covalent bonding, with biological ligands chosen among peptides and oligonucleotides.

22. The material according to claim 21, characterized in that it has a high density of biological ligands grafted on the surface of the nanoparticles, corresponding to more than 0.1 molecule of biological ligand per $nm^2$ of nanoparticles.

23. The material according to claim 21, characterized in that the nanoparticles are dissymmetric, so that at least 90% of the biological ligands are grafted on a continuous region representing less than 70% of the surface of the nanoparticle on which they are grafted.

24. The material according to claim 1, characterized in that the covalent bond between the nanoparticles and the biological ligands corresponds to a peptide or phosphate diester bond.

25. The material according to claim 1, characterized in that the size of the particles is within the range of 5 to 200 μm.

26. A growth method for oligonucleotides or peptides, characterized in that growth is performed on a material according to claim 1.

27. The method according to claim 26, characterized in that growth is performed in an automated synthesizer in which the support is confined in a cell by means of a filter through which flows of argon and reagents circulate alternately.

28. The method according to claim 27, characterized in that once growth is completed the covalent bond between the support and the nanoparticles is cleaved.

* * * * *